US00PP10850P

United States Patent [19]

Vijverberg

[11] Patent Number: Plant 10,850

[45] Date of Patent: Apr. 6, 1999

[54] CHRYSANTHEMUM PLANT NAMED 'VYRON'

[75] Inventor: Arnold Vijverberg, 's-Gravenzande, Netherlands

[73] Assignee: Vyking Flowers BV, Netherlands

[21] Appl. No.: 914,820

[22] Filed: Aug. 20, 1997

[51] Int. Cl.[6] ..... A01H 5/00

[52] U.S. Cl. ..... Plt./82.2

[58] Field of Search ..... Plt./82.2, 82.3

*Primary Examiner*—Howard J. Locker

*Attorney, Agent, or Firm*—Parkhurst & Wendel, L.L.P.

[57] ABSTRACT

A new and distinct cultivar of Chrysanthemum plant named 'Vyron', bearing medium sized yellow blooms with a brownish center and a performance of about 14 days.

2 Drawing Sheets

BACKGROUND OF THE INVENTION

The present invention comprises a new and distinct cultivar of Chrysanthemum plant which is a natural occurring sport of a parent Chrysanthemum named Regoltime (not patented). The new cultivar was discovered as a whole plant mutation in 1986 in a greenhouse at 's-Gravenzande in Holland. The invention has been asexually reproduced by cuttings at the same location. The new cultivar has been found to retain all of its distinctive characteristics through successive asexual propagations.

SUMMARY OF THE INVENTION

The present invention is a new and distinct variety of Chrysanthemum of a medium sized yellow bloom with a brownish center.

BRIEF DESCRIPTION OF THE DRAWINGS

The present invention of a new and distinct variety of chrystanthemum is shown in the accompanying drawings, the color being as nearly true as possible with color photographs of this type. In this regard, the ray florets illustrated in FIG. 2 appear slightly darker and more orange than true.

DESCRIPTION OF THE INVENTION

Figure 1:
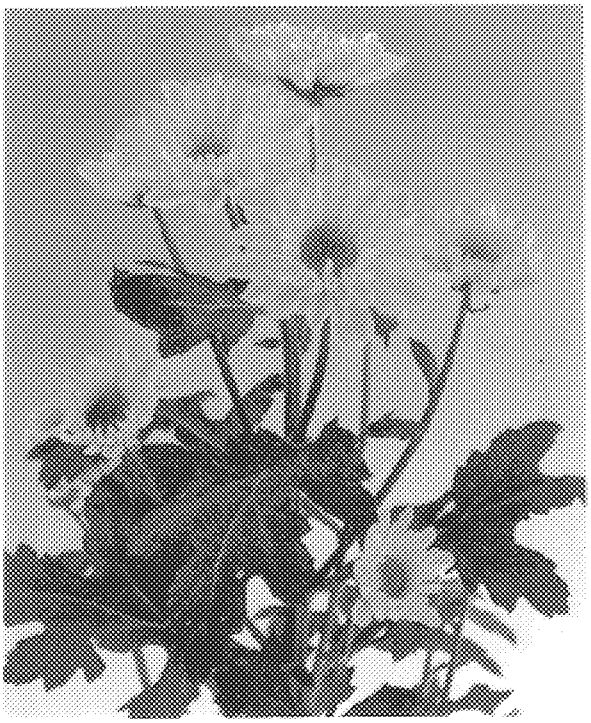
FIG. 1 shows a stem of the cultivar in full bloom.
Figure 2:
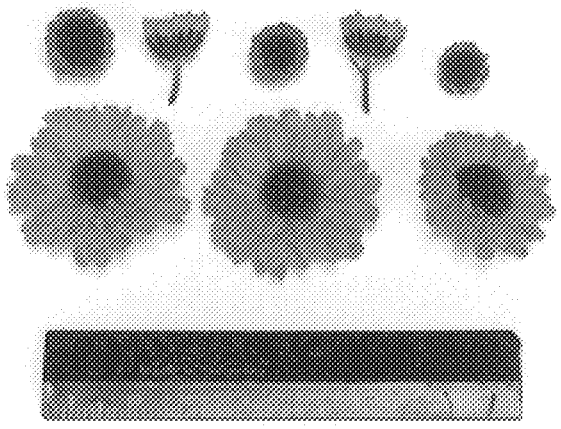
FIG. 2 shows the various stages of bloom of the new cultivar.
Figure 3:
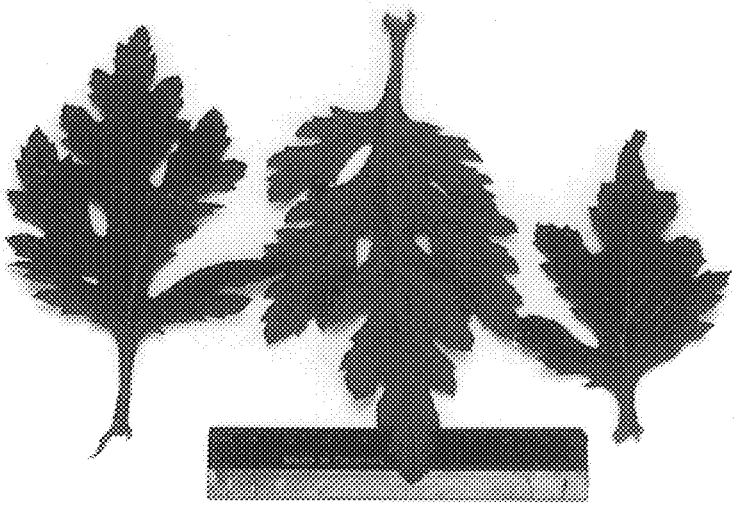
FIG. 3 shows foliage and petiole of the new cultivar.

This new variety of Chrysanthemum is of the botanical classification *Dendranthema grandiflora*. When grown in the vicinity of 's-Gravenzande, Holland, it has a response time of approximately 9 weeks. This new variety produces medium sized yellow blooms with a brownish center having a 2 week performance (i.e., vase life of 14 days). This new variety of chrysanthemum has been found to retain its distinctive characteristics throughout successive propagations and may be planted under greenhouse conditions in Holland between weeks 2 and 32.

The following is a description of the plant and characteristics (color designations are from R.H.S. Colour Chart) that distinguish it from related known varieties and antecedents: The color designations are taken from the plant itself. Accordingly, any discrepancies between the color designations and the colors depicted in the photographs are due to photographic tolerances.

| CULTIVAR | VYRON | PARENT CULTIVAR REGOLTIME |
|---|---|---|
| Color | | |
| Center of Flower/ Disc Floret | Immature: brown 200 B merging to yellow-orange at the edge Mature: greyed-orange 172A, deepening to the center | Immature: yellow-green 144A Mature: yellow-green 144C |
| Colour of the uppersurface of the majority of the ray-florets | Nearest Yellow 9A | Nearest Yellow 9A |
| Colour of the lowersurface of the majority of the ray-florets | Nearest Yellow 9B | Between Yellow 6C and Yellow 7C |
| Tonality from Distance | A yellow daisy with a brown center | A yellow daisy with a green center showing no pollen |
| Discoloration | none | to Yellow 8A |
| Pollen | none | none |
| Petals | | |
| Texture | Upperside smooth, underside smooth. | Upperside smooth, underside smooth. |
| Number | 55–65, three rows | 45–50, two rows |
| Cross-section | concave, one keel | convex, two keels |
| Arrangement | Imbricated | Imbricated |
| Persistence | Very good, petals keep straight total vaselife. | Very good, petals keep straight total vaselife. |
| Fragrance | Typical chrysanthemum | Typical chrysanthemum |
| Disc Diameter | medium (±1.7 cm) | medium (±1.5 cm) |
| Reproductive Organs | | |
| Stamen | Yellow-green, thick, ±5 mm in length. | Yellow-green, thick, ±5 mm in length. |
| Pollen | none | none |
| Styles | green, thick | green, thick |
| Sytle Length | ±5 mm | ±5 mm |
| Stigmas | yellow-green | yellow-green |
| Sigma Width | ±2 mm | ±2 mm |
| Ovaries | enclosed in calyx | enclosed in calyx |

-continued

| CULTIVAR | VYRON | PARENT CULTIVAR REGOLTIME |
|---|---|---|
| Plant | | |
| Form | Spray mum meant for erect culture. Herbaceous. | Spray mum meant for erect culture. Herbaceous. |
| Growth Height | short to medium ±100 cm | short ±100 cm |
| Stem Color | near green 137 A | yellow-green 146C |
| Stem Strength | strong to very strong | strong |
| Stem Brittleness | present | absent |
| Stem Anthocyanin Coloration | present | absent |
| Internodes | short, 2 cm | very short to short, 1½–2 cm |
| Flowering Response | 9 weeks | 10 weeks |
| Foliage | | |
| Color | upperside between 137 A and yellow-green 147 A, underside near green 137 C | upperside green 137 A, underside green 137 C |
| Size | length ±11 cm, width ±7 cm | length ±12 cm, width ±8 cm |
| Quantity | 26–30 | 28–32 |
| Shape | lobed, see photograph | lobed |
| Texture | upperside fleshy, underside smooth, slightly hirsute | upperside fleshy, underside smooth, slightly hirsute |
| Ribs and Veins | Ribs well developed, veins not so developed | Ribs well developed, veins not so developed |
| Edge | crenated | crenated |
| Shape of Base of Sinus Between Lateral Lobes | round | round |
| Margin of Sinus Between Lateral Lobes | converging | converging |
| Shape of Base | truncate | cordate |
| Apex | mucronate | cuspidate |
| Growth | | |
| Difference in average length | 0 | 0 |

-continued

| CULTIVAR | VYRON | PARENT CULTIVAR REGOLTIME |
|---|---|---|
| Response time | | |
| Difference in days of average response | 0 | 0 |
| Year of Discovery | 1986 | 1980 |
| A botanical description of Vyron and its parent Regoltime: | | |
| Bud | | |
| Size | large cross section 1.5 cm height ±1.2 cm | large cross section ±1.5 cm height ±1.2 cm |
| Form | round and flat | round and flat |
| Outside Color | near yellow-orange 15B | near yellow 7C |
| Bloom | | |
| Size | medium | small |
| Fully Expanded | 5–5½ cm | 4½–5 cm |
| Borne | Upper portion single flower per peduncle, lower portion plural flower per peduncle. | Upper portion single flower per peduncle, lower portion plural flower per peduncle. |
| Number of Blooms per Stem per Spray | average 8 | average 8 |
| Peduncle Lengths | Near the top ±6 cm Near the middle ±12 cm Near the bottom ±16 cm | Near the top ±6 cm Near the middle ±12 cm Near the bottom ±16 cm |
| Peduncle Lateral Shoot, Attachment | medium | medium |
| Peduncle Lateral Shoot, Angle | medium | small |
| Form | single (daisy) | single (daisy) |
| Performance | reasonable, 14 days (18–20° C.) | reasonable, 14 days (18–20° C.) |

I claim:

1. A new and distinct variety of Chrysanthemum plant as described and illustrated.

* * * * *